United States Patent
Mohr et al.

(12) 
(10) Patent No.: US 6,348,309 B1
(45) Date of Patent: *Feb. 19, 2002

(54) PROCESS FOR INACTIVATING VIRUSES IN BLOOD AND BLOOD PRODUCTS

(75) Inventors: Harald Mohr, Hannover; Bernd Lambrecht, Springe, both of (DE)

(73) Assignee: Blutspendedienst der Landesverbaende des Deutschen Roten Kreuzes Niedersachsen, Oldenburg und Bremen G.G.m.b.H. (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 788 days.

(21) Appl. No.: 08/751,624

(22) Filed: Nov. 18, 1996

Related U.S. Application Data

(63) Continuation-in-part of application No. 08/170,026, filed on Dec. 20, 1993, now abandoned, which is a continuation-in-part of application No. 07/838,282, filed as application No. PCT/DE90/00691 on Sep. 8, 1990, now abandoned.

(30) Foreign Application Priority Data

Sep. 13, 1989 (DE) .......................................... 39 30 510

(51) Int. Cl.$^7$ .................................................. A01N 1/02
(52) U.S. Cl. .......................................... 435/2; 424/529
(58) Field of Search ........................... 435/2, 299, 311; 424/89, 90, 529; 210/435, 645, 650, 651, 654, 656, 660, 679, 692; 604/4, 5, 6, 252, 406, 408, 410, 414

(56) References Cited

U.S. PATENT DOCUMENTS

| | | | | |
|---|---|---|---|---|
| 3,765,536 A | * | 10/1973 | Rosenberg | 210/446 |
| 4,181,128 A | * | 1/1980 | Swartz | 128/207.21 |
| 4,190,542 A | * | 2/1980 | Hodgson et al. | 210/282 |
| 4,728,432 A | * | 3/1988 | Sugiyama et al. | 210/646 |
| 4,878,891 A | * | 11/1989 | Judy et al. | 604/5 |
| 4,950,665 A | | 8/1990 | Floyd | 514/222.8 |
| 5,571,666 A | * | 11/1996 | Floyd et al. | 435/2 |

FOREIGN PATENT DOCUMENTS

| | | | |
|---|---|---|---|
| AU | 63391/90 | * | 4/1991 |
| EP | 0 196 515 A1 | | 10/1986 |

OTHER PUBLICATIONS

Heinmets, F. Inactivation of Viruses in Plasma by Photosensitized Oxidation, WRAIR-53-55 Research Report, Nov. 1955.*

Biorad Catalog Life Science Research Products, Bio-Rad, 1993.*

Schnipper L., Mechanisms of Photodynamic Inactivation of Herpes Simplex Viruses, J. Clinical Investigation 65(2)432-438, Feb. 1980.*

* cited by examiner

*Primary Examiner*—Ralph Gitomer
(74) *Attorney, Agent, or Firm*—Paula D. Morris & Associates, P.C.

(57) ABSTRACT

A process for inactivating viruses in blood and blood products in which a phenothiazine dye is added to the blood or blood product, and then irradiated with light. The use of a very small concentration of phenothiazine dye avoids any substantial adverse effects on the blood or blood products. Inactivation of the virus is effected by irradiation of the blood or blood product. After irradiation, the dye can be separated from the blood or blood product by a dye adsorbing agent.

24 Claims, 4 Drawing Sheets

PROCESS FOR INACTIVATING VIRUSES IN BLOOD AND BLOOD PRODUCTS

This application is a continuation-in-part of U.S. patent application Ser. No. 08/170,026 filed Dec. 20, 1993, now abandoned as a continuation in part of Ser. No. 07/838,282 filed Mar. 4, 1992 now abandoned. Ser. No. 07/838,282 is a national patent application deriving from International Application Serial No. PCT/DE90/00691 filed Sep. 8, 1990 and claiming priority from German Patent Application Number P 39 30510.4 filed Sep. 13, 1989.

This invention is directed to a process for inactivating viruses in blood or blood products, comprising: adding a phenothiazine dye to the solutions or suspensions to be treated and subsequently irradiating said phenothiazine dye-containing solutions or suspensions with visible light in the range of the adsorption peak of the respective dye whereafter the blood or blood products may be passed over an adsorbing agent for removal of the dye.

FIG. 1 of the accompanying drawings is a graph of time v. inactivation of human immunodeficiency virus (HIV-1) by the method of this invention.

Figure 1:
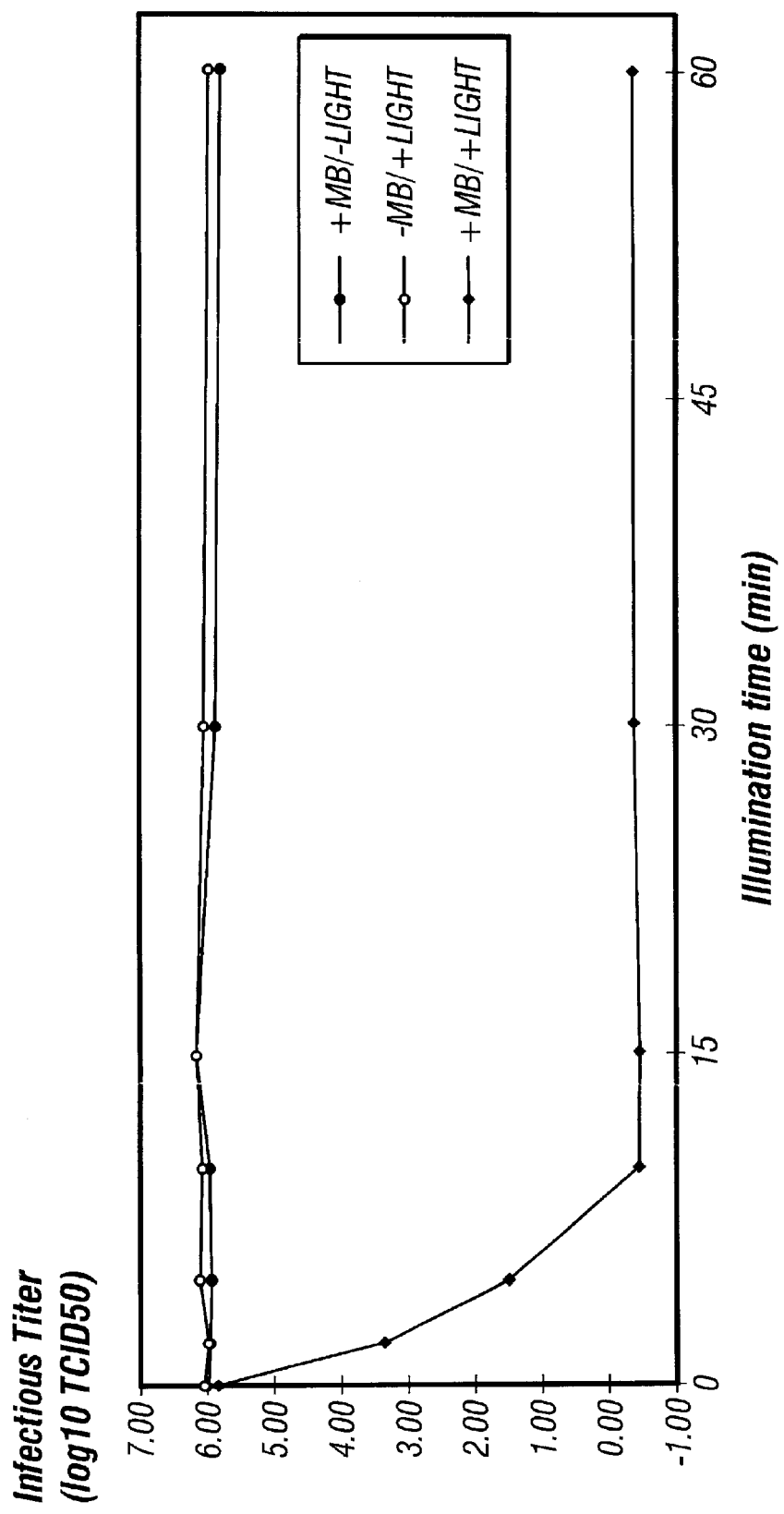

It is known that photodynamic substances in combination with visible or ultraviolet light may have a virus inactivating effect. This is due to the affinity of these substances to external virus structures or to the viral nucleic acid. Heinmets, F. et al, Inactivation of Viruses in Plasma by Photosensitized Oxidation, Walter Reed Research Report 53–55 (1955) showed that Eastern equine encephalomyelitis (EEE) virus in plasma was inactivated by various phenothiazine dyes at a dye concentration of 10 $\mu$M on activation with visible light. Toluidine blue 0 at a concentration of 2.5 $\mu$M effectively inactivated EEE virus in plasma in 1 minute using a 1000 watt light source in a special apparatus, whereas lesser dye concentrations failed to inactivate the virus completely.

Phenothiazine dyes react with membrane structures of enveloped viruses and damage the same irreversibly under the action of light, whereby the virus looses its infectiousness (cf. Snipes, W. et al, 1979, Photochem. and Photobiol. 29, 785–790). However, photodynamic substances also interact with viral RNA or DNA, especially with the guanine residues. When a dye/nucleic acid-complex has been formed, it is stimulated by light energy so that denaturation of the nucleic acid and finally strand breakages result. The reason is that phenothiazine dyes cause the conversion of molecular oxygen to activated species (singlet oxygen, oxygen radicals, etc.) which are highly reactive and may have various virucidal effects (cf. Hiatt, C. W., 1972, in: Concepts in Radiation Cell Biology, pp. 57–89, Academic Press, New York; Oh Uigin et al, 1987, Nucl. Acid. Res. 15, 7411–7427).

In contrast to other photodynamic dyes for virus inactivation, phenothiazine dyes, particularly methylene blue (MB), neutral red, thionine, and toluidine blue (TB) are of special interest because they may, in combination with visible light, inactivate a number of viruses, including some viruses which do not possess a lipid envelope, e.g. adenovirus. Other photoactive dyes, e.g. azure A, azure B, azure C, merocyanin 540, hematoporphyrin IX dihydrochloride, aluminum phthalocyanine chloride, acridine orange, and psoralens may also be useful.

In addition to that, MB and TB for instance, have themselves been used therapeutically, among other uses also as antidotes to carbon-monoxide poisoning and in long-term therapy of psychotic diseases. In this connection, quantities of MB or TB much higher than those required for virus inactivation are used (1 to 2 mg/kg of body weight) without any significant side effects. The low toxicities of MB and TB are also substantiated by data obtained from animal experiments.

However, since 1955, those skilled in the art have assumed that dye concentrations especially in the case of TB, of less than 2.5 $\mu$M, have only an insufficient virus inactivating effect (cf. F. Heinmets et al, 1955, Joint Report with the Naval Medical Research Institute, Walter Reed Army Institute of Research, U.S.A.).

In the previously described investigations of virus inactivation with phenothiazine dyes, the dye concentrations are between 10 $\mu$M and 100 $\mu$M (Chang and Weinstein, 1975, Photodynamic Inactivation of Herpes virus Hominis by Methylene Blue. Proceedings of the Society for Experimental Biology and Medicine 148, 291–293; Yen and Simon, 1978, Photosensitization of Herpes Simplex Virus Type 1 with Neutral Red, J. gen. Virol., 41, 273–271). At these concentrations, there arises the drawback that not only viruses may be inactivated, but also plasma proteins such as the coagulation factors, may be damaged. This is one of the reasons why phenothiazine dyes have so far not achieved any significance for virus inactivation in blood or blood products.

It is an object of the subject invention to provide a method in which various kinds of viruses are killed by the use of selected phenothiazine dyes without substantial functionally detrimental effects on the plasma proteins. It is a further object of the subject invention that the said process be of simple design, such that blood or blood products may be subjected to direct treatment in commercially available blood bags. At the low level concentrations of dye used in such treatment, removal of the dye is not necessary. However, a method is provided so that the added dyes may be removed after treatment if so desired.

The specified objects are accomplished in accordance with the invention in that these dyes are used at a concentration of from about 0.1 to about 2 $\mu$M, preferably from about 0.5 to 2 $\mu$M, and irradiation is effected directly in transparent containers, for example, blood bags of the kind used for collection and storage of blood or blood products.

Irradiation is performed either with daylight of sufficient intensity or an electric light, preferably from a cold light source, at a wavelength in the range of the absorption peak of the respective dye. Also, the following conditions should be observed for virus inactivation in blood plasma or plasma protein solutions. The operating temperature should range from 0° to 37° C., preferably from 4° to 20° C. The inactivating time may range from 2 minutes to 5 hours, preferably from 5 minutes to 3 hours, and pH should be between 5 and 9, preferably between pH 6 and pH 8.

An outstanding advantage of the process of this invention lies in its simplicity. F. Heinmets et al (as specified above) describe a highly complex apparatus through which, for instance, blood plasma must be passed. Here, problems of maintenance and above all capacity problems occur. Surprisingly, it has now been found that substantially smaller amounts of dye than that used in the prior art are sufficient for substantially complete inactivation of many viruses and that no complex technical apparatus is required for photoinactivation of viruses in blood or blood products.

Unexpectedly, it has also been found that non-enveloped viruses, such as adenovirus, which are normally resistant to photodynamic treatment, could be made photo-sensitive by a freezing/thawing step and subsequently could be inactivated in accordance with this invention. Inactivation has been successfully carried out irrespective of the order of freezing/thawing steps and addition of the dye. Freezing here means a deep-freezing operation at temperatures from about −20° C. to about 80° K. Normally, deep-freezing is carried out at or below −30° C.

Virus inactivation may be carried out directly in blood or plasma bags although these are transparent only to a limited extent. It is merely necessary to add the dye. Then the bag inclusive of its contents is exposed to light, whereafter the respective product may be used or further processed.

In one specific embodiment of the invention, the process is carried out in two interconnected containers, preferably containers suitable for collecting and storing blood or plasma. A separating column containing an agent for selectively absorbing the phenothiazine dye is interposed in the connecting passageway between the containers so that the dye is removed from the blood or plasma as it passes from the first container to the second container.

Thus, the process can be carried out without any major technical effort and is excellently suited for integration in the processing of individual blood donations. The small quantity of the dye used may either remain in the treated fluid or may be removed by adsorbing agents.

Suitable blood or blood products include:

whole blood red cell concentrates platelet concentrates plasma serum cryoprecipitate concentrates of coagulation factors inhibitors cold insoluble globulin albumin fibrinogen immune globulin.

The following examples illustrate the efficacy of the method of this invention for the inactivation of enveloped viruses generally and the inactivation of specific non-enveloped viruses. Except for Example 2, the tests were carried out at normal room temperature (22° C.).

EXAMPLE 1

Varying concentrations of MB in human plasma containing approximately $5 \times 10^7$ Plaque Forming Units (PFU) per ml of vesicular stomatitis virus (VSV). Control samples did not contain any dye. The sample volume was 0.5 ml. Control sample 1 and MB-containing samples 1 to 7 were irradiated with visible light for 4 hours at room temperature (22° C.); the others were stored in the dark at room temperature for the same length of time. The light source used was a slide projector equipped with a halogen bulb of 150 W (Osram Xenophot). The distance between the slide projector lens, i.e. the light outlet, and the samples was 30 cm in these tests.

Following completion of irradiation, the virus titer was determined in all samples by means of a plaque assay. The indicator cells used were BHK cells (Kidney, Syrian (Golden Hamster)). Results are shown in Table I.

TABLE I

| Samples | MB concentration in sample (μm) | Light | Virus Inactivation Factor |
|---|---|---|---|
| Control 1 | 0 | Yes | 4.8 |
| 1 | 0.01 | Yes | 11.8 |

TABLE I-continued

| Samples | MB concentration in sample (μm) | Light | Virus Inactivation Factor |
|---|---|---|---|
| 2 | 0.1 | Yes | 28.5 |
| 3 | 0.5 | Yes | $>10^6$ |
| 4 | 1 | Yes | $>10^6$ |
| 5 | 10 | Yes | $>10^6$ |
| 6 | 50 | Yes | $>10^6$ |
| 7 | 100 | Yes | $>10^6$ |
| Control 2 | 0 | No | 1 |
| 8 | 1 | No | 1 |
| 9 | 10 | No | 5 |
| 10 | 50 | No | 11.8 |
| 11 | 100 | No | 95 |

The results show that the infectious titer of VSV was reduced by irradiation by a factor of more than 6 $\log_{10}$ (log10) at MB concentrations above 0.5 μM indicating complete inactivation of VSV.

EXAMPLE 2

The following test confirmed complete or substantially complete virus inactivation at low concentrations of MB in human blood plasma.

In the presence of plasma and varying amounts of MB in aliquots of 500 μl, VSV (titer $4 \times 10^4$ PFU per ml) was irradiated overnight in a cold-storage room at 4° C. with the slide projector of Example 1 from a distance of 30 cm. Samples A to F were irradiated, sample G was not.

The results of this test are presented in Table II. They show that under the above-mentioned conditions VSV used was completely inactivated as indicated by a factor of more than 4 $\log_{10}$ (log10). The concentration of MB required was 0.5 μM.

It is probable that the VSV titer had already been reduced by 1 to 2 logs by the overnight incubation at 4° C. (39,2° F.), which would explain the relatively low initial titer. However, this hypothesis was not simultaneously tested.

A comparison of A (exposed) and G (dark) shows that light alone evidently does not influence the infectiousness of the virus to any great extent even after prolonged illumination.

TABLE II

| Sample | Final MB concentration μM | Titer/200 μl | Inactivation factor |
|---|---|---|---|
| A | 0 | $2 \times 10^4$ | 2.2 |
| B | 0.01 | $2.4 \times 10^4$ | 1.8 |
| C | 0.05 | $2 \times 10^4$ | 2.2 |
| D | 0.25 | $3 \times 104$ | 147 |
| E | 0.5 | ≦1 | $≦4.4 \times 10^4$ |
| F | 1.0 | ≦1 | $≦4.4 \times 10^4$ |
| G | 0 | $4.4 \times 10^4$ | 1 |

EXAMPLE 3

The photoinactivation of viruses in the presence of phenothiazine dyes depends on the light exposure time. To find out what exposure times would be sufficient for photoinactivation of VSV in the presence of 0.5 μM MB, $10^6$ Plaque Forming Units (PFU) of virus per ml were suspended in plasma and irradiated as in Example 1 for different periods of time at 22° C. The results are listed in Table III. It is evident that under the specified test conditions an exposure time of one hour was sufficient to reduce the infectious VSV titer by a factor of more than 6 $\log_{10}$ ($\log_{10}$), indicating complete deactivation.

TABLE III

| Sample | Exposure time (min) | Inactivation factor |
|---|---|---|
| control | 0 | 1 |
| 1 | 5 | 50 |
| 2 | 30 | 1666 |
| 3 | 60 | >10$^6$ |

EXAMPLE 4

Vesicular Stomatitis Virus (VSV) in plasma (4×10$^3$ PFU/ml) was irradiated with white light at room temperature using the same light source as in Example 1 in the presence of 1 μM of TB. The results listed in Table IV show complete deactivation of the virus as indicated by reduction of the infectious VSV titer by a factor greater than 4 times 3 $\log_{10}$ (log10).

TABLE IV

| Sample | Exposure time (min) | Inactivation factor |
|---|---|---|
| control | 0 | 1 |
| 1 | 10 | 20 |
| 2 | 60 | > 4 × 10$^3$ |

EXAMPLE 5

In the following examples the influence of MB/light treatment on the AIDS virus HIV-1 was investigated. Dye concentration was 1 μM; the initial virus titer was about 10$^6$ infectious particles per ml. Viral infectivity was assayed using MT-4 cells (an HTLV-1 infected human T-lymphoblastoid cell line). Virus titers (as in the other examples below) are expressed as $\log_{10}$ (log10) TCID$_{50}$ (TCID—Tissue Culture Infective Dose). The plasma volume was 76 ml, and it was illuminated in a 75 cm$^2$ polystyrene tissue culture flask. The illumination device used was an air cooled light bank equipped with 8 fluorescent tubes 115 W, Philips, TL-M 115 W/33 RS, Double Flux), emitting light at an intensity of about 45,000 Lux. The results of these examples are listed in Table 5. It is evident that HIV-1 is especially sensitive to MB/light treatment: Viral infectivity was reduced by approx. 6 $\log_{10}$ (log10) steps within the first 10 minutes of light exposure and below the detection limit of the assay used. It becomes also evident that the dye alone or illumination in the absence of dye were not detrimental to the virus.

TABLE V

| | $\log_{10}$ TCID$_{50}$/ml HIV-1 | | |
|---|---|---|---|
| Exposure time (min) | Sample A MB | Sample B Light | Sample C MB + Light |
| 0 | 6.00 | 6.06 | 5.82 |
| 2 | 5.94 | 6.00 | 3.37 |
| 5 | 5.94 | 6.12 | 1.5 |
| 10 | 5.94 | 6.06 | ≦0.5 |
| 15 | 6.06 | 6.12 | ≦0.5 |
| 30 | 5.76 | 5.94 | ≦0.5 |
| 60 | 5.70 | 5.82 | ≦0.5 |

EXAMPLE 6

Tests similar to that described in Table V were conducted with a number of other viruses. The results of these investigations are summarized in Table VI. As indicated by the symbol >, in most cases viral infectivity could be reduced below the detection limit of the assay applied.

TABLE VI

| Virus | Family | Characteristics | Inactivation Rate ($\log_{10}$ TCID$_{50}$) | Illumination Time (min) |
|---|---|---|---|---|
| Enveloped Viruses | | | | |
| HIV-1 | Retro | ssRNA | >6.50 | 10 |
| HIV-2 | Retro | | >3.81* | 15 |
| SIV | Retro | | >6.26* | 15 |
| Herpes Simplex | Herpes | dsDNA | >5.50* | 60 |
| Bovine Herpes | Herpes | | >8.11* | 30 |
| Suid Herpes Type 1 | Herpes | | 4.43* | 60 |
| Sindbis | Toga | ssRNA | >9.73 | 5 |
| West Nile | Flavi | | >6.50 | 60 |
| Hog Cholera | Flavi | | >5.92* | 5 |
| Semliki Forest | Toga | | >7.00 | 10 |
| Vesicular Stomatitis | Rhabdo | ssRNA | >4.89* | 60 |
| Influenza | Orthomyxo | ssRNA | 5.10 | 60 |
| Non-enveloped Viruses | | | | |
| Calici | Calici | ssRNA | >3.9 * | 5 |
| SV40 | Papova | dsDNA | >4.00 | 30 |

In all those cases outlined in Table VI in which the resulting inactivation rates are marked by an *, the inactivation experiments were conducted under "production conditions", i.e. the plasma was in a plastic bag and its volume was between 250 and 300 ml. The results indicate that there is no problem to inactivate viruses under these conditions.

EXAMPLE 7

In general, there was no success in attempts to inactivate non-enveloped viruses under the conditions used and in the presence of at least 80% plasma. Two exceptions (Calicivirus and SV40) are shown in Table VI. Using adenovirus, it was investigated whether a prolonged pre-incubation period (at 4° C. in the dark) in the presence of the photoactive dye (1 μM MB) led to increased sensitivity of the virus. Sample volume was 4 ml. Illumination time was affected for 30 minutes using halogen bulbs (light intensity: 150,000 Lux). Virus was titrated on FL cells. As Table VII indicates, regardless of the pre-incubation time, there was no change in viral infectivity.

When, instead of MB, TB was used under the same conditions, the virus titer was also not reduced by photodynamic treatment.

TABLE VII

| Sample | Pre-Incubation Time | Dye | Virus titer ($\log_{10}$ TCID$_{50}$) |
|---|---|---|---|
| control | 0 h | — | 6.0 |
| 1 | 0 h | MB | 6.0 |
| 2 | 1 h | MB | 5.5 |
| 3 | 4 h | MB | 6.0 |
| 4 | 24 h | MB | 6.0 |

EXAMPLE 8

It was found out that at least partial inactivation of adeno-virus can be achieved when a freeze/thaw (F/T) step is integrated into the procedure consisting of addition of the photosensitizer, pre-incubation for 1 h and illumination. The freezing temperature was −30° C., thawing was in a water bath at 27° C. As Table VIII indicates, it is important that the F/T step precedes illumination. It is of secondary importance whether the photo-sensitizer is added prior to or after freezing/thawing the plasma.

TABLE VIII

| Sample | Sample Treatment | Virus Titer (Log$_{10}$ TCID$_{50}$) |
|---|---|---|
| Control | Untreated | 7.5 |
| A | F/T | 7.0 |
| B | F/T + 60 min irradiation | 7.5 |
| C | F/T + MB + 60 min pre-incubation + 60 min irradiation | 2.5 |
| D | MB + F/T | 7.5 |
| E | MB + F/T + 10 min irradiation | 5.0 |
| F | MB + F/T + 30 min irradiation | 5.0 |
| G | MB + F/T + 60 min irradiation | 4.0 |

EXAMPLE 9

A special problem when using high dye concentrations is in the immediate effect of these substances on plasma proteins. Therefore, the influence of different dye concentrations on the activities of coagulation factors was investigated.

Varying amounts of MB were added to human plasma (2 ml aliquots). The activities of the coagulation factors V, VIII, and IX were measured immediately thereafter. As is evident from Table IX, said factors are inhibited in all three cases in dependence on the concentration of the dye, whereby the activities of the factors VIII and V are inhibited from about 10 $\mu$M and those of factor IX already from 2.5 $\mu$M. Consequently, at higher concentrations, MB has a direct effect on the proteins without need of the action of light.

TABLE IX

| Methylene Blue ($\mu$M/l) | Factor V E/ml | Factor VIII E/ml | Factor IX E/ml |
|---|---|---|---|
| 0 | 0.80 | 0.38 | 2.0 |
| 1 | 0.76 | 0.41 | 1.9 |
| 2.5 | 0.78 | 0.41 | 1.6 |
| 5 | 0.74 | 0.38 | 1.45 |
| 10 | 0.54 | 0.35 | 1.20 |
| 20 | 0.44 | 0.28 | 1.10 |

EXAMPLE 10

Not only the dye concentration, but also the exposure time influences the activities of coagulation factors. This time-dependence has been determined for varying concentrations of MB.

Samples of human plasma (aliquots of 2 ml) received varying amounts of MB and were then exposed to light for 1 to 4 hours (as described in Example 1). Control samples were not subjected to photo-treatment. As is evident from Table X, the activities of the three coagulation factors V, VIII, and IX are inhibited in dependence on time and the concentration of the dye. Especially in the cases of factors VIII and IX, higher MB concentrations and exposure times from 2 hours upwards cause an apparent increase in their thrombolytic activities.

TABLE XI

| Light Exposure Hours | MB Concentration $\mu$M/l | Factor V E/ml | Factor VIII E/ml | Factor IX E/ml |
|---|---|---|---|---|
| 0 h | 0 | 0.86 | 0.33 | 1.20 |
|  | 1 | 0.86 | 0.45 | 1.20 |
|  | 2.5 | 0.82 | 0.33 | 0.46 |
|  | 10 | 0.72 | 0.30 | 0.44 |
| 1 h | 0 | 0.84 | 0.40 | 0.76 |
|  | 1 | 0.72 | 0.24 | 0.92 |
|  | 2.5 | 0.68 | 0.24 | 0.82 |
|  | 10 | 0.47 | 0.16 | 0.68 |
| 2 h | 0 | 0.82 | 0.44 | 0.10 |
|  | 1 | 0.64 | 0.23 | 0.90 |
|  | 2.5 | 0.68 | 0.22 | 0.72 |
|  | 10 | 0.60 | 0.15 | 0.74 |
| 4 h | 0 | 0.76 | 0.38 | 0.98 |
|  | 1 | 0.56 | 0.16 | 0.94 |
|  | 2.5 | 0.49 | 0.29 | 0.82 |
|  | 10 | 0.42 | 0.27 | 0.64 |

EXAMPLE 11

In accordance with a preferred embodiment of the subject invention, the photoinactivation of viruses may be effected directly in the plasma bag. The dye at an effective concentration is merely added to the blood or the blood products and then the bag is exposed to light for the appropriate time. In this simple way it is possible at any time to treat blood products from indi- vidual donors.

In a test which mimicked routine treatment of plasma, two plastic bags containing human plasma which had been stored at −30° C. were thawed in a water bath at 27° C. The plasma was then inoculated with VSV. The resulting infectivity of the virus containing plasma was 5.61 $\log_{10}$ (log10) TCID$_{50}$.

MB was added to the plasma at a final concentration of 1 $\mu$M. After pre-incubating in the dark for 1 h, the plasma units were placed on the light bank equipped with fluorescent tubes described before and illuminated for different times at room temperature. At each time point, samples were taken to determine the virus titer. The results listed in Table XI show that in both cases under the conditions described, the infections titer of VSV could be reduced by more than 5 $\log_{10}$-steps with 60 minutes.

TABLE XI

Infectious Titer (log$_{10}$ TCID$_{50}$)

| Sample | Illumination Time (min) | Plasma Unit 1 | Plasma Unit 2 |
|---|---|---|---|
| Control | after thawing | 5.61 | 5.61 |
| 1 | 0 | 5.37 | 5.25 |
| 2 | 5 | 3.59 | 3.34 |
| 3 | 10 | 2.92 | 2.45 |
| 4 | 15 | 2.33 | 1.49 |
| 5 | 30 | 1.31 | 0.60 |
| 6 | 60 | 0.36 | 0.18 |

EXAMPLE 12

Figure 2:
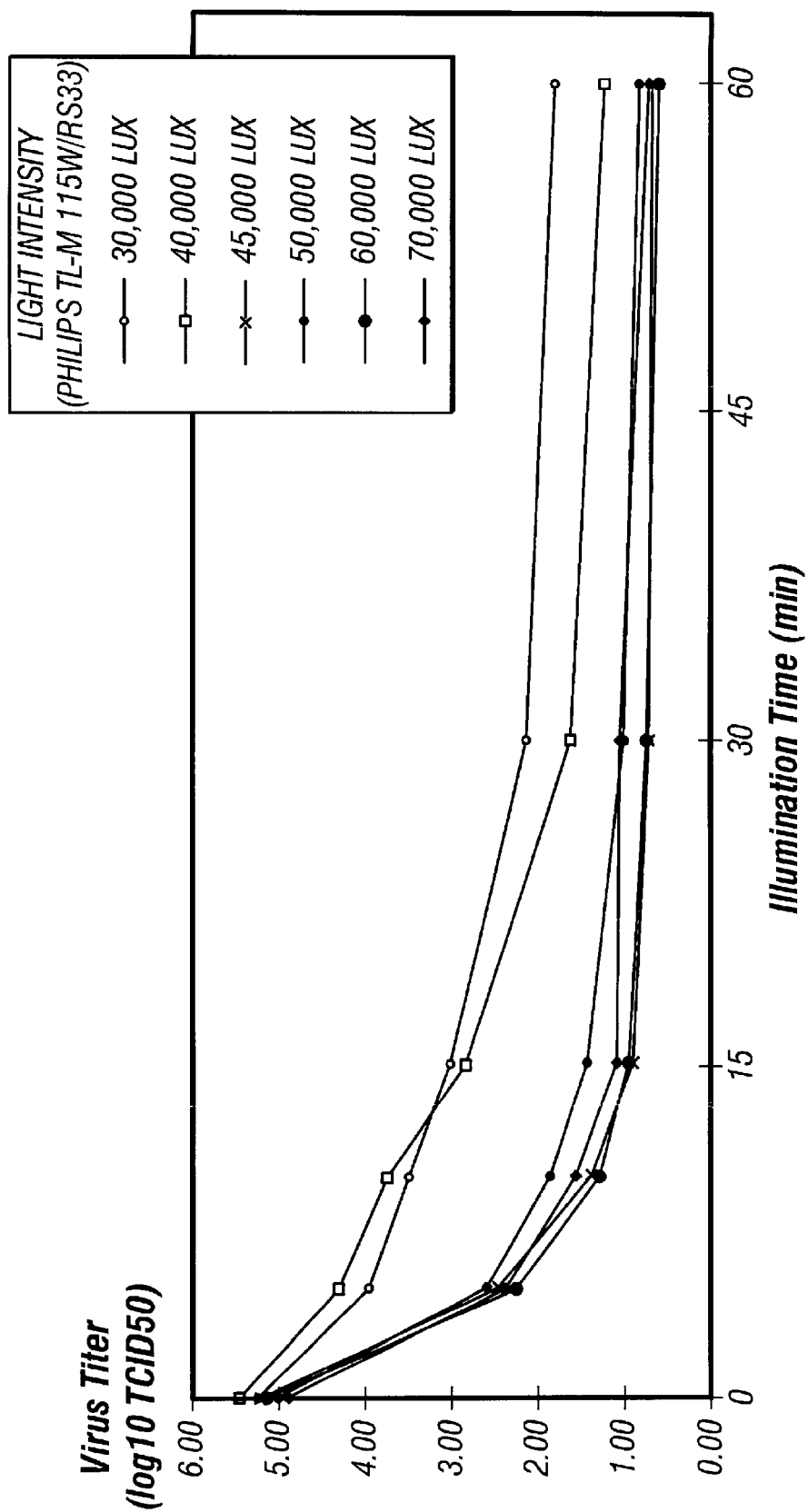
FIG. 2 is a graph illustrating the influence of light intensity on the inactivation of vesicular stomatitis virus (VSV) by the method of this invention.

In the foregoing examples, different light sources were used, having different light intensities. To investigate more systematically how this parameter influences virus inactivation, VSV containing plasma was illuminated in the presence of 1 $\mu$M MB at light intensities between 30,000 and 70,000 Lux. The illumination device used was again the light bank mentioned equipped with fluorescent tubes. The plasma was in plasma bags, and its volume was approx. 250 ml. As can be seen from FIG. 2, there exists a close correlation between the light intensity applied and the efficacy of photodynamic treatment. Whereas illumination at 30,000 Lux resulted in only partial inactivation of VSV even after 60 min., viral infectivity was almost completely reduced to the detection limit of the assay within 15–30 min. when the light intensity was above 60,000 Lux.

EXAMPLE 13

In the preceding examples, it was shown that viruses in plasma can successfully be inactivated by photodynamic treatment. It was of interest to know whether the same approach might be used to decontaminate platelet suspensions which are more turbid and consequently not as transparent as plasma alone. In these tests, the sample volume was 4 ml, platelet concentration in plasma was $3 \times 10^8$ / ml ($3 \times 10$ to the power of 8), and the test virus was VSV. Dye concentration in the suspensions was 1 $\mu$M. Besides MB, also other phenothiazine dyes were tested, namely TB and the demethylated derivatives of MB, azure A, B, C, and thionine, respectively. All these dyes have similar light absorption maxima, ranging between about 595 nm for thionine and approx. 660 nm for MB. Accordingly, in all cases the same light source could be used for illumination, i.e. the light bank described in Example 5 with fluorescent tubes.

Figure 3:
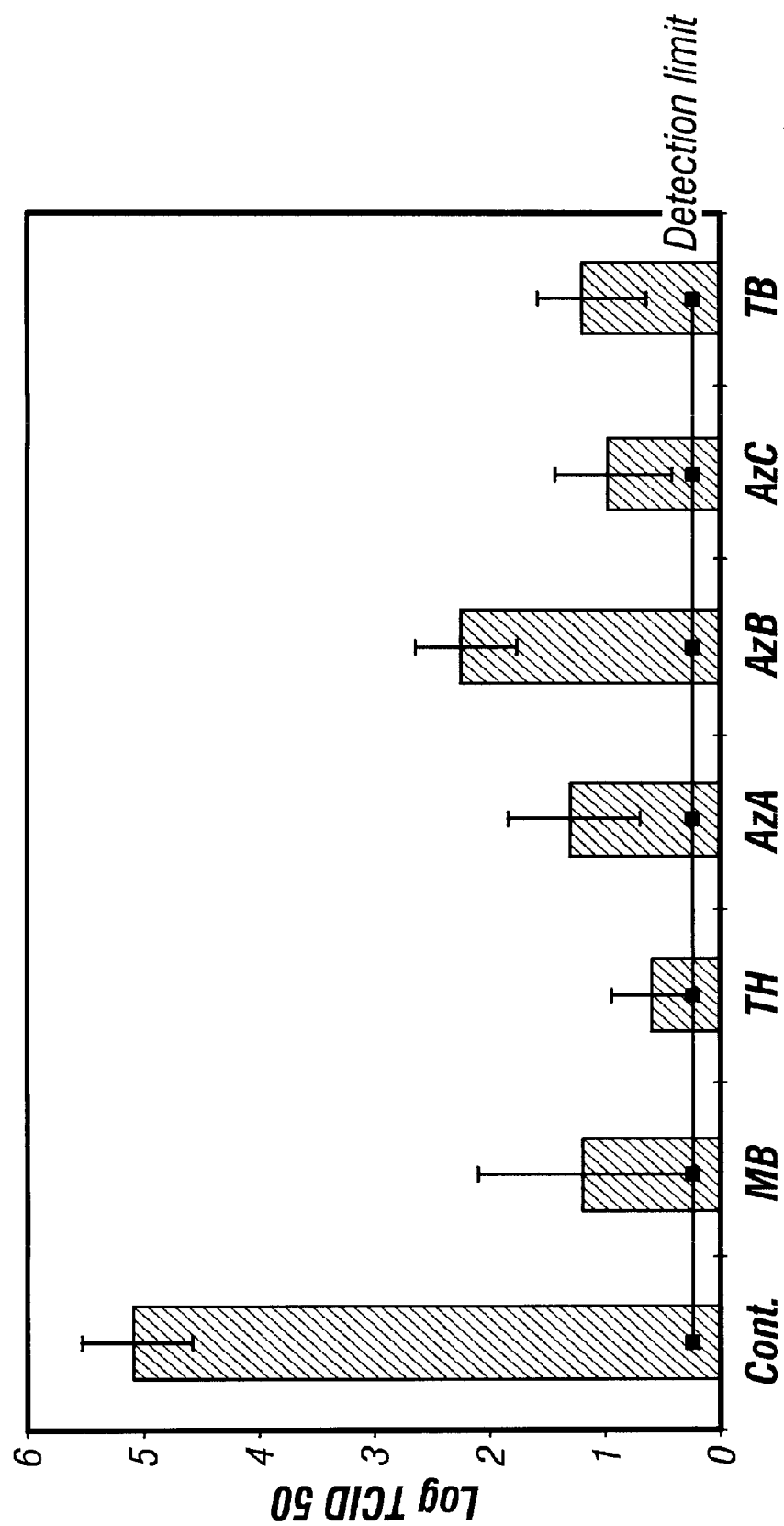
FIG. 3 is a bar graph showing the efficacy of various pheno-thiazine dyes for photodynamic inactivation of VSV in platelet suspensions at dye concentrations of 1 $\mu$M in each specimen and an irradiation time of 30 minutes.

The results depicted in FIG. 3 illustrate that regardless of the photosensitizer used, viral infectivity could be considerably reduced. Thionine (Th), azure A (AzA), azure C (AzC), and TB were of similar efficacy as MB. Another result of these tests is that the same procedure which works in plasma might be used for platelet suspensions.

The phenothiazine dyes used for virus inactivation may remain in the blood or the blood products, particularly at the concentrations used here, without side effects occurring. However, they may be subsequently removed by means of dialysis, gel filtration, or adsorption.

Of the specified methods, the adsorptive ones are of main interest because they require the least effort as to time and technical apparatus, and the respective plasma protein solutions are not diluted.

However, some adsorbing agents are obviously unsuitable, such as the ion exchangers mentioned by Hiatt (Concepts in Radiation Cell Biology, pp. 57–89, Academic Press, New York, 1972) because in addition to the dye they also strongly bind plasma proteins, such as coagulation factors.

In order to use an adsorbing agent to remove the dye, the blood or blood product simply is passed over the adsorbing agent. Suitable adsorbing agents include, but are not necessarily limited to those selected from the group consisting of porous glass, silica gel, polystyrene-divinylbenzene, and acrylic ester polymers having a pore size in the range of from about 10 Å to about 300 Å.

Surprisingly, it has now been found that MB and other phenothiazine dyes bind very strongly to a various commercially available separation gels, including those which either do not or only weakly bind proteins. Such adsorbing agents are therefore especially suitable for the later removal of the photo-oxidant. Of the adsorbing agents tested, the following ones may be used for the removal of MB and other phenothiazine dyes.

| Adsorbing Agent | Material | Manufacturer or Supplier |
| --- | --- | --- |
| Daltosil 75 | Modified Silica Gel | Serva, Heidelberg, FRG |
| Si 100-Polyo | Derivatized Silica | Serva, Heidelberg, FRG |

-continued

| Adsorbing Agent | Material | Manufacturer or Supplier |
| --- | --- | --- |
| RP18 | Gel containing $C_{18}$-groups | |
| Kieselgel 40 | Silica Gel | Merck, Darmstadt, FRG |
| Nucleosil 50 Å pore size | Silica Gel | Macherey & Nagel, Dueren, FRG |
| Nucleosil 100 Å pore size | Silica Gel | Macherey & Nagel, Dueren, FRG |
| Vydac SC-201 RP | Glass beads coated with Silica Gel bearing $C_{18}$-groups | Macherey & Nagel, Dueren, FRG |
| CPG 40 | Controlled pore (porous glass beads) | Pierce Europe, FRG |
| Bio Beads | Polystyrene DVB (Divinylbenzene) | Bio Rad, Muenchen, FRG |
| Amberlite adsorbent resins | Polyacrylester | Roehm & Haas, Frankfurt, FRG |

In most cases, 2 g of the respective adsorbing agent, used as a batch, were sufficient at a feed concentration of 10 $\mu$M MB to completely extract the dye from 250 ml of a plasma protein solution.

Two types of adsorbing agents proved to be particularly suitable:

1. Silica gels having pores so small a size (40 to approximately 300 Å diameter) that plasma proteins cannot penetrate the gel matrix while the low molecular weight dye molecules can do so and are thus bonded thereto due to ionic, electrostatic and hydrophobic interaction.

Examples of commercially available adsorbing agents of this type are Matrex Silica Gel (Amicon, Witten), Daltosil (Serva, Heidelberg), and Kieselgel (Merck, Darmstadt).

2. Gels of the type based on polystyrene divinylbenzene and acrylic ester polymer, respectively. They, too, are manufactured with suitable pore sizes.

Examples of commercially available gels of these types are Amber-lite (Roehm & Haas, Frankfurt, among others) and Bio Beads (Bio Rad, Munchen). They are mainly used to remove non-polar substances or surface-active agents such as detergents from aqueous solutions. They are either non-polar or only slightly polar.

EXAMPLE 14

MB was added to 250 ml fresh plasma. The final dye concentration was 10 $\mu$M 5 ml aliquots received varying amounts of Daltosil (pore size 75 Å) and Bio Beads SM16 (pore size 144 Å), respectively, and were then stirred for 30 minutes. Then the gel was left to settle.

In the plasma the factor VIII and factor V contents, extinction at 660 nm and, for some samples, the protein contents were measured. The results of the investigation are shown in Table XII.

TABLE XII

| | E (660 nm) | Protein (mg/ml) | Factor VIII (U/ml) | Factor V (U/ml) |
| --- | --- | --- | --- | --- |
| Fresh plasma | 0.909 | 66.8 | 1.10 | 1.20 |
| Fresh plasma + MB | 1.450 | 65.6 | 0.42 | 0.96 |
| Daltosil | | | | |
| 50 mg | 0.576 | — | 0.60 | 1.05 |
| 100 mg | 0.571 | — | 1.10 | 1.10 |
| 250 mg | 0.491 | — | 1.10 | 1.20 |
| 500 mg | 0.477 | 66.8 | 1.25 | 1.20 |

TABLE XII-continued

| | E (660 nm) | Protein (mg/ml) | Factor VIII (U/ml) | Factor V (U/ml) |
|---|---|---|---|---|
| Bio Beads SM 16 | | | | |
| 50 mg | 0.666 | — | 0.82 | 1.05 |
| 100 mg | 0.571 | — | 1.05 | 1.10 |
| 250 mg | 0.571 | — | 1.05 | 1.10 |
| 500 mg | 0.530 | 72.5 | 0.80 | 1.15 |

It is evident from the extinction values that apparently further substances in addition to the dye are extracted from the plasma. But these substances are not plasma proteins. The extinction values of the plasma which had been treated with 100 to 250 mg of adsorbing agent per 5 ml, i.e. with 2–5 weight percent (% w/v), hardly differ from those which had been extracted with 10% w/v adsorbing agent. Hence, at an MB concentration of 10 $\mu$M 2–5% w/v of adsorbing agent are sufficient in both cases for removing the dye from the plasma in a batchwise operation. If the feed concentration of the dye is lower, the amount of adsorbing agent required is correspondingly lower.

EXAMPLE 15

In a further test, a 5 percent human serum albumin solution (5% HSA) was used instead of blood plasma. Again, the MB concentration was 10 $\mu$M. Aliquots of 5 ml were extracted batchwise with 100 mg, respectively, of the following adsorbing agents for varying periods of time: Daltosil (pore size 75 Å), Kieselgel (pore size 40 Å), and Bio Beads SM16 (pore size 144 Å).

Figure 4:
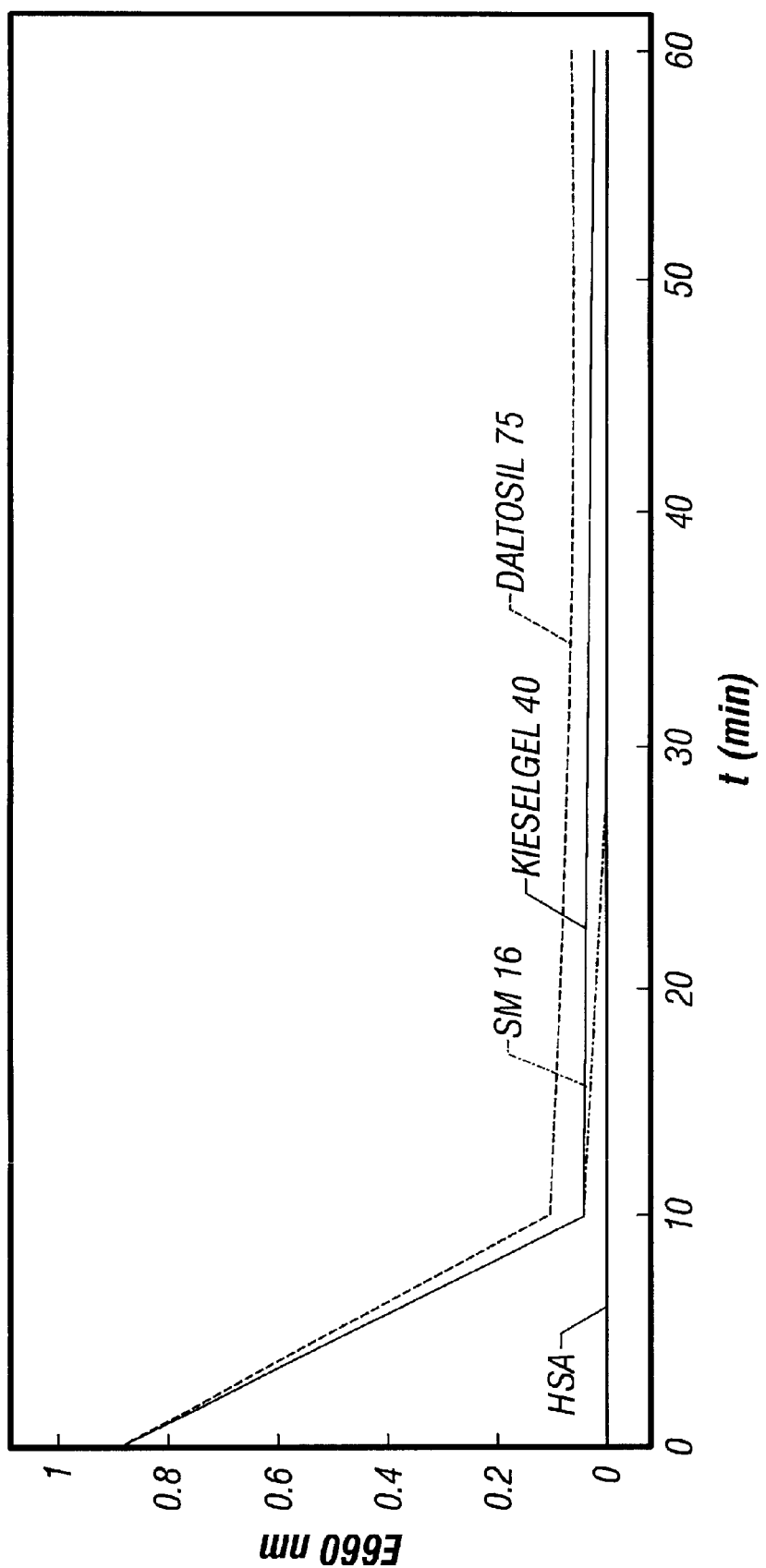
FIG. 4 is a graph showing the rate of adsorption of methylene blue from a 5% albumin solution by various adsorbents.

As shown in FIG. 4, the extinction at 660 nm decreases to a constant value in all three cases within a period of 20 to 30 minutes, i.e. this time period is sufficient to remove the photo-oxidant in batches from a plasma protein solution. As is further evident from FIG. 4, Bio Beads SM16 and Kieselgel 40 appear to be somewhat better adsorbing agents in the subject case than Daltosil with a pore size of 75 Å.

EXAMPLE 16

The aim of this test was to find out whether or not the adsorptive removal of the photo-oxidant can also be effected by chromatography. This was based on the idea of carrying out the virus inactivation by means of a dye in combination with light in a container, such as a blood bag, and in turn transferring the plasma protein solution to another container, such as a second blood bag, via a small separating column interposed between said containers, and containing the adsorbing agent. If the assembly, comprising the first bag, the adsorbing column, and the second bag were prefabricated so that a closed system were available, it would be possible in a very simple way and at the minimum risk of contamination to produce virus-inactivated plasma protein preparations, including from single donor units.

To this end, 250 ml of 5% albumin solution were passed at varying flow rates through a separating column containing 5 ml of Kieselgel (pore size 40 Å). Fractions of 10 ml each were collected and their extinction was measured at 660 nm. As can be seen from Table XIII, the overall volume of the albumin solution may be passed through the column at flow rates of 5 and 7.5 ml/min, respectively, and no MB residues could be detected in the fractions leaving the column. Hence, the time required for removal of the dye from 250 ml of solution is only 30 to 35 minutes at most.

The test result shows that the removal of the photo-oxidant by chromatography may be effected without any problems, and also proves that the above-mentioned production of virus-inactivated plasma protein preparations from single donor units is indeed possible.

TABLE XIII

| Starting Material - MB extinction (660 nm): 0.067 Fraction No. | Flow Rate 5 extinction | (ml/min) 7.5 (660 nm) |
|---|---|---|
| 1 | 0.002 | 0.001 |
| 3 | 0.000 | 0.001 |
| 5 | 0.000 | 0.002 |
| 7 | 0.002 | 0.003 |
| 9 | 0.001 | 0.001 |
| 11 | 0.000 | 0.001 |
| 13 | 0.000 | 0.001 |
| 14 | 0.002 | 0.001 |

What is claimed is:

1. A method for substantially completely inactivating viruses in a blood product, comprising:
   providing a blood bag comprising a transparent wall retaining said blood product comprising said viruses;
   adding to said blood bag a phenothiazine dye in an amount sufficient to produce a dye concentration in said blood product in the range of from about 0.5 $\mu$M to about 2 $\mu$M; and
   irradiating said blood bag and said blood product comprising phenothiazine dye retained therein with visible light having a wavelength in the range of the absorption peak of said phenothiazine dye, wherein said irradiation passes through said transparent wall to said phenothiazine dye and continues for a period of time sufficient to substantially completely inactivate said viruses.

2. The method of claim 1 wherein said blood product is plasma.

3. The method of claim 2 wherein said substantially complete inactivation comprises a reduction of infectious titer by a factor of at least about 6 $\log_{10}$.

4. The method of claim 1 wherein said blood product is infected with an enveloped virus.

5. The method of claim 4 wherein said substantially complete inactivation comprises a reduction of infectious titer by a factor of at least about 6 $\log_{10}$.

6. The method of claim 1 wherein the phenothiazine dye is methylene blue.

7. The method of claim 6 wherein said substantially complete inactivation comprises a reduction of infectious titer by a factor of at least about 6 $\log_{10}$.

8. The method of claim 1 wherein the phenothiazine dye is toluidine blue.

9. The method of claim 1 wherein the phenothiazine dye is azure A.

10. The method of claim 1 wherein the phenothiazine dye is azure B.

11. The method of claim 1 wherein the phenothiazine dye is azure C.

12. The method of claim 1 wherein the phenothiazine dye is thionine.

13. The method of claim 1 wherein the virus is Type 1 Human Immunodeficiency virus.

14. The method of claim 1 wherein the virus is the Type 2 Human Immunodeficiency virus.

15. The method of claim 1 wherein the blood product contains a non-enveloped virus.

16. The method of claim 15 wherein the blood product is subjected to deep freezing at or below −30° C. and then thawed prior to irradiation.

17. The method of claim 16 wherein the dye is added prior to the freezing step.

18. The method of claim 1 wherein after said irradiating said dye is removed from said blood product by an adsorbing agent for said dye.

19. The method of claim 1 wherein said substantially complete inactivation comprises a reduction of infectious titer by a factor of at least about 6 $\log_{10}$.

20. A method for removal of phenothiazine dye from a blood product, said method comprising passing said blood product over an adsorbing agent which strongly binds said phenothiazine and only weakly binds blood proteins, said adsorbing agent being selected from the group consisting of, silica gel, polystyrene-divinylbenzene, acrylic ester polymers having a pore size in the range of from about 10 Å to about 300 Å, and combinations thereof.

21. A method for substantially completely inactivating viruses in a blood product, comprising:

providing a transparent container retaining said blood product comprising said viruses;

adding to said transparent container a phenothiazine dye in an amount sufficient to produce a dye concentration in said blood product in the range of from about 0.5 µM to about 2 µM; and irradiating said transparent container and said blood product comprising phenothiazine dye retained therein with visible light having a wavelength in the range of the absorption peak of said phenothiazine dye for a period of time sufficient to substantially completely inactivate said viruses.

22. The method of claim 21, wherein said substantially complete inactivation comprises a reduction of infectious titer by a factor of at least about 6 $\log_{10}$.

23. A method for substantially completely inactivating viruses in a blood product comprising:

providing a blood bag comprising a transparent wall retaining said blood product comprising said viruses;

adding to said blood bag an amount of phenothiazine dye sufficient to substantially completely inactivate said viruses upon exposure of said blood bag to sufficient irradiation, said amount of said dye being insufficient to cause substantial detrimental effects on plasma proteins in said blood product; and irradiating said blood bag and said blood product comprising phenothiazine dye retained therein with visible light having a wavelength in the range of the absorption peak of said phenothiazine dye, wherein said irradiation passes through said transparent wall to said phenothiazine dye and continues for a period of time sufficient to substantially completely inactivate said viruses.

24. The method of claim 23, wherein said substantially complete inactivation comprises a reduction of infectious titer by a factor of at least about 6 $\log_{10}$.

* * * * *